United States Patent
Kenney

Patent Number: 5,916,814
Date of Patent: Jun. 29, 1999

[54] PRESEALED INTEGRAL HEMATOCRIT TEST ASSEMBLY AND METHOD

[75] Inventor: James W. Kenney, Broomall, Pa.

[73] Assignee: Drummond Scientific Company, Broomall, Pa.

[21] Appl. No.: 08/728,055

[22] Filed: Oct. 9, 1996

[51] Int. Cl.⁶ .................................................. G01N 33/86
[52] U.S. Cl. ........................... 436/70; 436/165; 436/177; 422/58; 422/59; 422/73; 422/99; 422/102; 422/104; 422/918; 600/370; 600/573; 73/61.65; 73/61.68
[58] Field of Search .............................. 436/70, 165, 174, 436/177, 45; 422/58, 59, 68.1, 72, 73, 99, 102, 104, 918; 128/760, 763; 73/61.41, 61.65, 61.66, 61.68; 600/368, 370, 573

[56] References Cited

U.S. PATENT DOCUMENTS

| | | | |
|---|---|---|---|
| 3,684,161 | 8/1972 | Unger et al. | 494/17 |
| 3,706,306 | 12/1972 | Berger et al. | 600/575 |
| 3,783,696 | 1/1974 | Coleman | 73/864.02 |
| 3,914,985 | 10/1975 | von Behrens | 73/61.72 |
| 3,958,045 | 5/1976 | Coleman | 427/230 |
| 4,028,930 | 6/1977 | Moreno | 73/61.66 |
| 4,052,164 | 10/1977 | Konig | 422/72 |
| 4,052,165 | 10/1977 | Wienchol et al. | 422/72 |
| 4,648,265 | 3/1987 | Sarstedt | 73/61.65 |
| 4,835,106 | 5/1989 | Johnson et al. | 436/45 |
| 4,854,170 | 8/1989 | Brimhall et al. | 73/570 |
| 4,956,298 | 9/1990 | Diekmann | 435/293.1 |
| 4,963,326 | 10/1990 | Eberle | 422/101 |
| 5,059,398 | 10/1991 | Kenney | 422/100 |
| 5,065,768 | 11/1991 | Coleman et al. | 600/573 |
| 5,230,864 | 7/1993 | Columbus | 422/100 |
| 5,242,660 | 9/1993 | Hsei | 422/102 |
| 5,257,984 | 11/1993 | Kelley | 604/403 |
| 5,277,873 | 1/1994 | Hsei | 422/102 |
| 5,279,150 | 1/1994 | Katzer et al. | 73/61.66 |
| 5,286,454 | 2/1994 | Nilsson et al. | 422/102 |
| 5,316,952 | 5/1994 | Brimhall | 436/70 |
| 5,422,018 | 6/1995 | Saunders et al. | 436/45 X |
| 5,456,885 | 10/1995 | Coleman et al. | 422/101 |
| 5,460,782 | 10/1995 | Coleman et al. | 422/100 |
| 5,472,671 | 12/1995 | Nilsson et al. | 422/102 |
| 5,556,599 | 9/1996 | Ahmed | 422/102 |

*Primary Examiner*—Maureen M. Wallenhorst
*Attorney, Agent, or Firm*—John F. A. Earley; John F. A. Earley, III; Harding, Earley, Follmer & Frailey

[57] ABSTRACT

A presealed integral hematocrit test assembly includes a holder, a bore molded into the holder, and a blood sample tube mounted on the holder adapted to receive a sample of blood by capillary action, whereby the blood sample tube is filled with blood from its inlet end by capillary action, and the test assembly is centrifuged into a column having a red corpuscles portion, white corpuscles portion, and a plasma portion. The method of using the presealed integral hematocrit test assembly includes the steps of measuring the length of the red cells column portion and measuring the total length of the blood column, and dividing the length of the red cells column portion by the total length of the blood column to make the hematocrit determination.

8 Claims, 1 Drawing Sheet

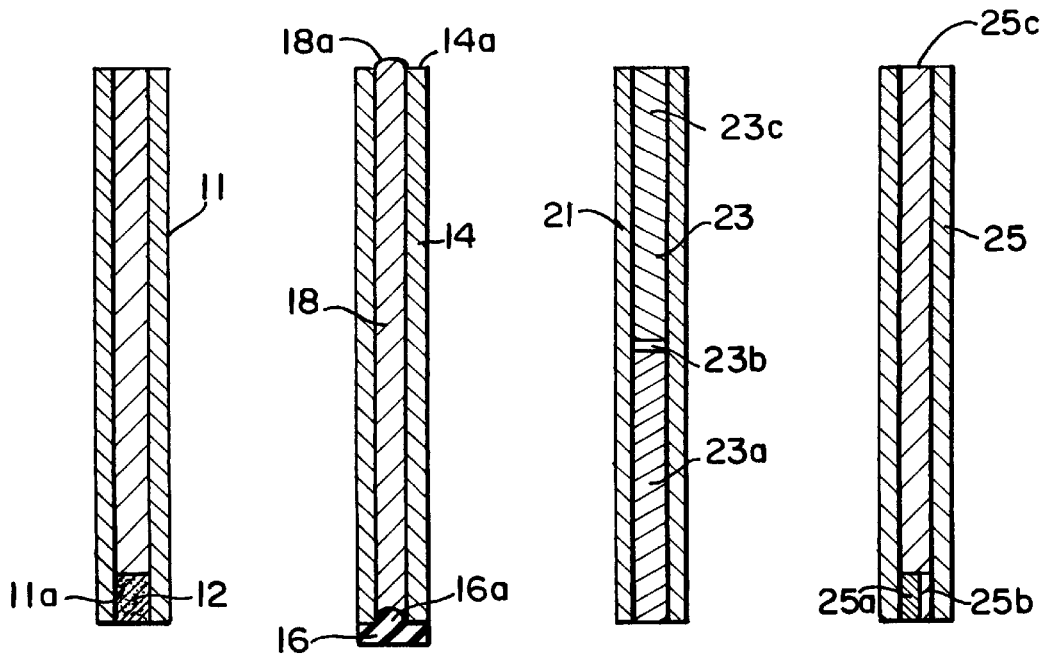
FIG. 1 PRIOR ART
FIG. 2 PRIOR ART
FIG. 3 PRIOR ART
FIG. 4 PRIOR ART
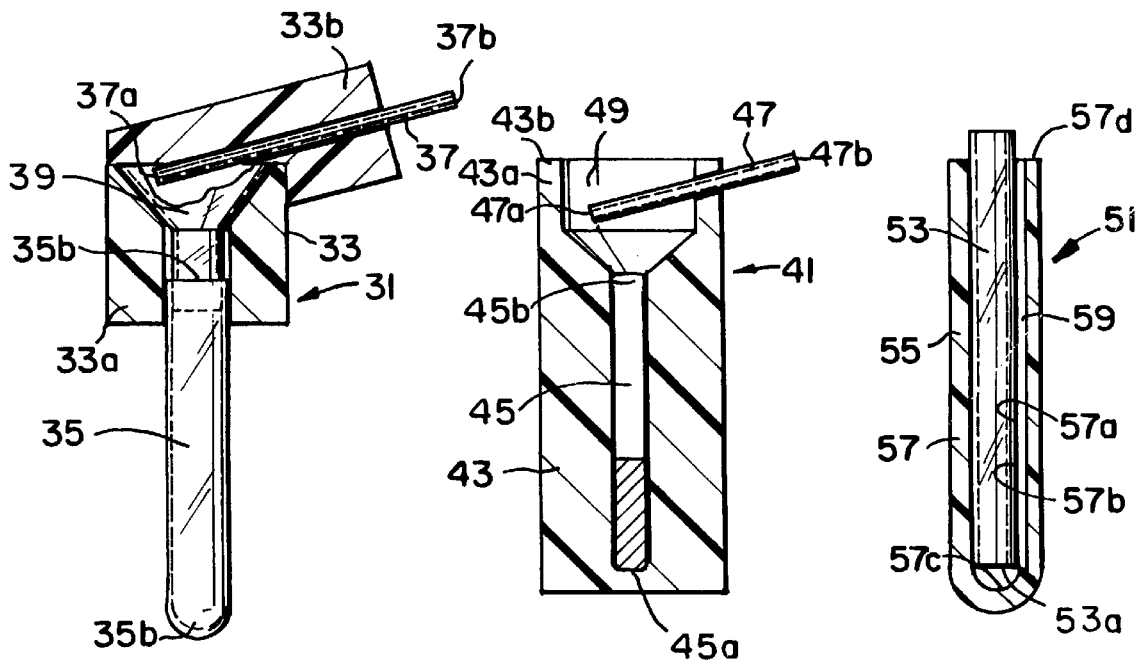
FIG. 5
FIG. 6
FIG. 7
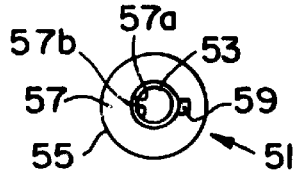
FIG. 8

PRESEALED INTEGRAL HEMATOCRIT TEST ASSEMBLY AND METHOD

BACKGROUND OF THE INVENTION

1. Technical Field

This invention relates to the field of blood sampling and testing, and more particularly concerns making a hematocrit determination from a blood sample, especially before giving blood as a blood donor.

2. Background of the Prior Art

Before you are allowed to donate blood, like to the Red Cross, a hematocrit determination must be made, which is the ratio of the volume of red cells to the total volume of the blood sample.

One method of testing the blood has been to check the specific gravity of the blood by putting a drop of blood into a copper sulfate solution. If the drop of blood falls to the bottom, it means that the blood has a higher specific gravity than the copper sulfate solution. If the blood sample floats, it means that the blood should be checked further.

In testing blood to make a hematocrit determination, the ratio of volume of red cells to the total volume of the blood sample, it is conventional to take a capillary blood sample tube, prick the finger or ear of a patient to produce a drop of blood, draw the blood into a blood sample tube by capillary action, and send the blood sample out to a laboratory which makes the hematocrit determination, and reports back to the doctor or blood sample technician who had ordered the test. This procedure may take several days, which is undesirable.

Accordingly, it has been a problem to provide quicker and cheaper ways of making a hematocrit determination. This search has been intensified with the advent of desk-top portable centrifuges which have now become available.

In order to shorten the time necessary to make a hematocrit determination, it is now possible to provide the technician who takes the blood sample with a portable centrifuge so that the technician can immediately make a hematocrit determination. This is very useful when the patient is a potential blood donor because the technician can make an instantaneous determination before the blood donor gives blood, and the blood donor is not left sitting around for a long period of time while awaiting the hematocrit determination.

In making this instant hematocrit determination, one prior art procedure is to prick the finger or ear of a potential blood donor, or patient, to produce a drop of blood, draw the blood into a blood sample capillary tube by capillary action, place the filled sample tube into a chamber in a holder with the bottom end of the tube in contact with a rubber seal or plug to hold the blood from discharging from the bottom of the tube, place the holder into a centrifuge, turn on the centrifuge and separate the blood into a column with a red cells column portion at the bottom of the tube, a white cells column portion in the middle of the tube, and a blood plasma column portion at the top of the tube. Then the hematocrit determination is made immediately by dividing the length of the red cells column portion by the total length of the blood column.

This on-the-spot hematocrit determination procedure requires use of device which has two separate parts, the sample tube and the holder which receives the sample tube, and requires the insertion of the bloody blood sample tube into the holder. This can be awkward and cause a bloody mess. Also, the bottom end of the sample tube is supported by a bottom seal made of resilient rubber which pushes upwardly into the hollow bore of the sample tube to form a nipple therein which pushes a top portion of the blood upwardly to extend above the top end of the capillary sample tube. Then when the centrifuge spins, the top portion of blood which is above the end of the capillary sample tube is struck by air and is vaporized. This is undesirable.

BRIEF SUMMARY OF THE INVENTION

The present invention is designed to overcome the above problems. In particular, the present invention is designed to overcome the awkwardness of trying to insert a blood filled sample tube into a holder. Also, the present invention is designed to prevent the vaporization of a top portion of blood which extends above the tube in the centrifuge.

The objects of this invention are accomplished by providing a hematocrit test assembly having a blood sample tube and holder which are integral, with the holder having a bore that which is presealed at the bottom, and does not have a blood sample tube which is separate from the holder, so that there is no potentially messy transfer of a separate blood sample tube filled with blood into a holder.

BRIEF DESCRIPTION OF THE DRAWINGS

FIG. 1 is a view of a prior art blood sample tube with a clay plug seal in the bore of the tube at one end.

FIG. 2 is a view of prior art blood sample capillary tube as it is seated in a holder of a centrifuge with the bottom of the sample tube being seated on a rubber seal that forms a nipple that projects into the bottom of the tube and forces out a portion of the blood sample above the top of the tube.

FIG. 3 is a view of a prior art blood sample tube which has been centrifuged to form a column of blood having a red corpuscles portion at the bottom, a white corpuscles portion in the middle, and a plasma portion at the top.

FIG. 4 is a view of another prior art blood sample capillary tube with an end seal that is provided with a bore that vents the air when the blood is being drawn into the capillary tube by capillary action, and is closed by the blood contacting the end seal.

FIG. 5 is a view of a presealed integral hematocrit test assembly constructed in accordance with the present invention.

FIG. 6 is a view of another embodiment of the presealed integral hematocrit test assembly of this invention.

FIG. 7 is a view of another embodiment of the presealed integral hematocrit test assembly of this invention.

FIG. 8 is a top plan view of the inventive presealed hematocrit test assembly of FIG. 7.

DETAILED DESCRIPTION OF THE DRAWINGS

Turning now to the drawings, in the prior art testing of blood to make a hematocrit determination, the ratio of the volume of red cells to the total volume of the blood sample, referring to FIG. 1., one procedure has been to take a capillary blood sample tube 11, prick the finger or ear of a patient or potential blood donor to produce a drop of blood, draw the blood into the sample tube 11 by capillary action but leave empty an end portion 11a of the tube, jab the empty end portion 11a into a bed of clay to form an end seal 12 of clay that prevents the blood from flowing out of the blood sample tube 11 at end 11a, place the filled sample tube 11 into a holder, place the holder and sample tube 11 into a centrifuge, and centrifuge the blood sample into a column having a bottom red corpuscles portion, a middle white corpuscles portion, and a plasma portion. The hematocrit determination has been made by measuring the length of the red cells column portion, measuring the total length of the blood column, and dividing the length of the red cell column portion by the total length of the blood column.

But this procedure requires the insertion of a bloody sample tube 11 into a holder and this procedure can be awkward and can cause a bloody mess. Also, jabbing the tube into the clay can break the tube and cause jagged ends of the tube to cut the person doing the jabbing, which can and has caused AIDS.

Another prior art procedure is illustrated by FIG. 2 and the capillary blood sample tube 14, wherein the blood is drawn into the sample tube 14 by capillary action, and the bloody blood sample tube 14 is inserted into a chamber in a holder and the end of tube 14 is seated onto a rubber seal 16. The end of sample tube 14 compresses the perimeter of the rubber seal 16 and forces a rubber nipple 16a into the bottom of the blood column 18 which forces a portion 18a of the blood column 18 to project above the end 14a of blood sample tube 14. Because of this, the blood portion 18a is vaporized during the centrifuging operation as the air strikes portion 18a, and this is undesirable.

A view of a prior art capillary blood sample tube 21 is shown in FIG. 3 after centrifuging which produces a column of blood 23 having a bottom red corpuscles portion 23a, a middle white corpuscles portion 23b and a top plasma portion 23c.

FIG. 4 is a view of a capillary blood sample tube 25 having a bottom plug 25a with a small bore 25b formed in the plug 25a. The capillary blood sample tube 25 is filled with blood from its inlet end 25c and the air is vented from the blood sample tube 25 through bore 25b as this capillary action takes place. Then when the blood reaches the plug 25a, the blood closes the bore 25b on contacting the plug mixture.

A view of a presealed integral hematocrit test assembly 31 in accordance with this invention is shown in FIG. 5 and includes a holder 33 with a bore 35 having a closed bottom end 35a and an open top end 35b molded into the holder 33, and a capillary blood sample tube 37 fixedly mounted on the holder 33. Blood sample tube 37 is open at its bottom end 37a and open at its top inlet end 37b for receiving a blood sample by capillary action through its top inlet end 37b.

The holder 33, hematocrit bore 35, and blood sample tube 37 are all integral with each other.

The blood sample tube 37 is filled with blood from its inlet end 37b by capillary action, and the test assembly 31 is inserted into a centrifuge to spin the test assembly and its blood sample to centrifuge the blood sample into a column having a red corpuscles portion, a white corpuscles portion, and a plasma portion, for instant hematocrit determination.

Holder 33 has a first arm 33a and a second arm 33b, with the bore 35 being molded in the first arm 33a. The holder 33 is made of a clear plastic so that the blood sample in the bore 35 may be seen, and its portions may be measured.

Blood sample tube 37 is mounted on second arm 33b in such a matter that its bottom end 37a is positioned above the top end 35b of the bore 35 so that the sample of blood may be discharged from the bottom end 37a of the sample tube 37 into the top end 35b of the bore 35. An upper chamber 39 is provided in holder 33 beneath the bottom end 37a of blood sample tube 37 and above top end 35b of bore 35. Chamber 39 is funnel shaped and funnels the blood from sample tube 37 into the bore 35.

FIG. 6 is a view of another embodiment of the invention and shows a presealed integral hematocrit test assembly 41 with a holder 43, and a bore 45 with a closed bottom end 45a and an open top end 45b molded into the holder 43. A blood sample tube 47 is mounted in the top portion 43a of holder 43 and pierces the wall 43b that surrounds an upper chamber 49 of the holder 43.

Blood sample tube 47 is open at its bottom end 47a and is open at its top inlet end 47b for receiving a blood sample by capillary action through its top inlet end 47b. The holder 43, the bore 45, and the blood sample tube 47 are all integral with each other.

In operation, the blood sample tube 47 is filled with blood from its inlet end 47b by capillary action, and the test assembly 41 is inserted into a centrifuge to spin the hematocrit test assembly to centrifuge the blood sample from blood sample tube 47 into upper chamber 49 and bore 45, and to centrifuge the blood sample in bore 45 into a column having a red corpuscles portion, a white corpuscles portion, and a plasma portion, for instant hematocrit determination.

The method of using the presealed integral hematocrit test assemblies 31 and 41 comprises the steps of providing a presealed integral hematocrit test assembly 31, 41 which includes a holder 33, 43, having a bore 35, 45 with a sealed closed bottom end 35a, 45a and an open top receiving end 37b, 43b molded into the holder 33, 43, a blood sample tube 37, 47 fixedly mounted on the holder 33, 43, with the sample tube 37, 47 having an open top inlet end for receiving blood samples by capillary action through its top inlet end and having an open bottom discharge end for delivering the blood sample from the sample tube to the bore, with the holder 33, 43, bore 35, 45, and blood sample tube 37, 47 being integral with each other, drawing a drop of blood from a patient, touching the inlet end of the sample tube to the drop of blood filling the sample tube with the blood by capillary action, placing the presealed integral hematocrit test assembly into a centrifuge, spinning the hematocrit test assembly 31, 41 by actuating the centrifuge, discharging the blood sample from the sample tube 37, 47 into the bore 35, 45, and centrifuging the blood sample in the bore into a column having a column portion of red corpuscles, a column portion of white corpuscles, and a column portion of blood plasma.

Then the length of the red cells column portion is measured, total length of the blood column is measured, and the hematocrit determination is made by dividing the length of the red cells column portion by the total length of the blood column.

Another embodiment of the invention is shown in FIGS. 7 and 8 which disclose a presealed integral hematocrit test assembly 51 comprising a capillary blood sample tube 53 made of glass, a holder 55 having a holder case 57 which is made of clear plastic and which is molded around blood sample tube 53 and which has a bore 57a with an inner face 57b and a bottom end 57c. A vent passageway 59 is formed in the inner face 57b of holder case 57 and extends from the bottom end 57c of the bore 57a to the top 57d of bore 57a for allowing the passage of air from the bottom 53a of the blood sample tube 53 while it is drawing the blood into the blood sample tube 53 by capillary action.

The method of making a hematocrit determination from a blood sample using the test assembly 51 comprises the steps of providing a presealed integral hematocrit test assembly 51 which comprises a capillary blood sample tube 53 made of glass, a holder 55 having a holder case 57 which is made of a clear plastic and which is molded around blood sample tube 53 and which has a bore 57a with an inner face 57b and a bottom end 57c, and a vent passageway 59 which is formed in the inner face 57b of holder case 57 and extends from the bottom end 57c of the bore 57a to the top end 57d of bore 57a for allowing the passage of air from the bottom 53a of the blood sample tube 53 while it is drawing the blood into the blood sample tube 53 by capillary action, drawing a drop of blood from a patient, touching the inlet end of the sample tube to the drop of blood, filling the sample tube with the blood by capillary action, placing the presealed integral hematocrit test assembly 51 into a centrifuge, spinning the hematocrit test assembly 51 by actuating the centrifuge and centrifuging the blood sample in the blood sample tube 53 into a column having a column portion of red corpuscles, a column portion of white corpuscles, and a column portion of blood plasma, measuring the length of the red cells column portion, measuring the total length of the blood column, and dividing the length of the red cells column portion by the total length of the blood column to make the hematocrit determination.

ADVANTAGES

This invention has many advantages. For example, if you go to the Red Cross to donate blood, the technician just sticks your ear or your finger with a needle to provide a drop of blood, draws the blood into the sample tube by capillary action, and puts the presealed integral hematocrit test assembly of the invention into a small portable centrifuge machine right there at the table, spins the holder and centrifuges the blood sample into a red cells portion, a white cells portion, and a plasma portion, stops the centrifuge from spinning, and electronically projects the result on a screen, which the technician then reads. This gives the technician immediate feedback, and the blood sample does not have to be sent out to a laboratory and you do not have to wait for the results.

Also, the prospective blood donor does not have to sit around waiting for a hematocrit determination. The technician doing the interview and blood test immediately decides whether or not the prospective donor is or is not a valid donor.

The technician using the hematocrit test assembly of this invention does not have to assemble it, or try to put a bloody sample tube into a holder. The technician just holds onto the holder like a handle, touches the inlet end of the sample tube to the drop of blood, fills the tube, puts the integral test assembly into the centrifuge, and the centrifuge takes over.

The test assembly is inexpensive, and is used only once and is thrown away so that it is sanitary and does not require cleaning.

The technician who draws the blood by using the integral test assembly eliminates all handling of separate parts. He just takes the test assembly, fills the blood sample tube with blood, and puts the test assembly into the centrifuge machine. He then turns on the centrifuge machine and awaits the results which he reads on an electronic screen.

I claim:

1. A presealed integral hematocrit test assembly comprising
    a holder,
    a hematocrit bore with a closed bottom end and an open top end molded into the holder,
    said bore being straight,
    said bore being uniform in diameter,
    a blood sample tube fixedly mounted on the holder to make the tube integral with the holder and the hematocrit bore,
    said blood sample tube being open at a bottom end and open at a top inlet end for receiving a blood sample by capillary action through said top inlet end,
    wherein said bottom end of said sample tube is positioned above the open top end of the bore,
    said holder, hematocrit bore, and blood sample tube being fixedly connected together to be integral with each other,
    whereby the blood sample tube is filled with blood from said inlet end by capillary action to form a blood sample,
    and when the test assembly is inserted into a centrifuge to spin the hematocrit test assembly the blood sample is discharged from the sample tube through the bottom end thereof into the top end of the bore so as to centrifuge the blood sample in the bore into a column having a red corpuscles portion, a white corpuscles portion, and a plasma portion, for instant hematocrit determination.

2. The hematocrit test assembly of claim 1,
    the holder having a first arm and a second arm,
    the hematocrit bore being molded into the first arm of the holder,
    the holder being made of clear plastic so that a blood sample in the hematocrit bore may be seen,
    the blood sample tube being mounted on the second arm of the holder to make the tube integral with the holder and the hematocrit bore,
    the blood sample tube being mounted on the second arm so that said bottom end is positioned above the top end of the hematocrit bore so that the sample of blood collected into the blood sample tube is discharged from the bottom end of the sample tube into the top end of the hematocrit bore.

3. A presealed integral hematocrit test assembly comprising
    a holder having a first arm and a second arm,
    a bore with a closed bottom end and an open top end molded into the holder,
    said bore being straight,
    said bore being uniform in diameter,
    a blood sample tube fixedly mounted on the holder to make the tube integral with the holder and the bore,
    said blood sample tube being open at a bottom end and open at a top inlet end for receiving a blood sample by capillary action through said top inlet end and for discharging a blood sample from the blood sample tube through said bottom end,
    the blood sample tube being held in the second arm of said holder so that said bottom end is positioned above the top end of the bore so that a sample of blood collected into the blood sample tube is discharged from the bottom end of the sample tube into the top end of the bore,
    said holder, bore, and blood sample tube being integral with each other.

4. A hematocrit test assembly comprising
    a capillary blood sample tube having an open bottom end,
    a holder having a holder case molded around the sample tube,
    said holder case having a bore with an inner face and a closed bottom end,
    and a vent passageway formed in the inner face of the holder case and extending from the bottom end of the bore to a top of the holder to connect the bottom end of the bore to the top of the holder for allowing the passage of air from the open bottom end of the blood sample tube while the blood sample tube is drawing blood into the blood sample tube by capillary action to the top of the holder for discharging the air.

5. A method of making a hematocrit determination from a blood sample, comprising the steps of providing a presealed integral hematocrit test assembly which comprises a holder, a bore with a sealed closed bottom end and an open top receiving end molded into the holder, said bore being straight, said bore being uniform in diameter, a blood sample tube fixedly mounted on the holder to make the tube integral with the holder and the bore, said sample tube having an open top inlet end for receiving blood samples by capillary action through said top inlet end and having an open bottom discharge end for delivering a blood sample from the sample tube to the bore, wherein the bottom end of the sample tube is positioned above the open top end of the bore said holder, bore, and blood sample tube being integral with each other, drawing a drop of blood from a patient, touching the top inlet end of the sample tube to the drop of blood, filling the sample tube with the blood by capillary action, placing the presealed integral hematocrit test assembly into a centrifuge, spinning the hematocrit test assembly by actuating the centrifuge to discharge the blood from the sample tube into the bore, and centrifuging the blood sample in the bore into a straight column having a straight column portion of uniform diameter of red corpuscles, a straight column portion of uniform diameter of white corpuscles, and a straight column portion of uniform diameter of blood plasma, whereby a hematocrit determination is made by measuring a length of the relative straight column portions.

6. The method of claim 5, further including the steps of measuring a length of the red corpuscles column portion, and measuring a total length of all of the blood column portions, whereby a hematocrit determination is made by dividing the length of the red corpuscles column portion by the total length of all of the blood column portions.

7. A method of making a hematocrit determination from a blood sample, comprising the steps of providing a presealed integral hematocrit test assembly which comprises a holder, a bore with a closed bottom end and an open top end molded in the holder, said bore being straight, said bore being uniform in diameter, a blood sample tube mounted in the bore of the holder to make the tube integral with the holder and the bore, said blood sample tube being open at a bottom end and open at a top inlet end for receiving a blood sample by capillary action through said top inlet end, said holder, bore, and blood sample tube being integral with each other, drawing a drop of blood from a patient, touching the top inlet end of the sample tube to the drop of blood, filling the sample tube with the blood by capillary action, placing the presealed integral hematocrit test assembly into a centrifuge, spinning the hematocrit test assembly by actuating the centrifuge to discharge the blood sample from the sample tube into the bore, and centrifuging the blood sample in the bore into a column having a column portion of red corpuscles, a column portion of white corpuscles, and a column portion of blood plasma, whereby a hematocrit determination is made by measuring a length of the relative column portions.

8. The method of claim 7, further including the steps of measuring a length of the red corpuscles column portion, and measuring a total length of all of the blood column portions, whereby a hematocrit determination is made by dividing the length of the red corpuscles column portion by the total length of all of the blood column portions.

* * * * *